Feb. 26, 1963 L. H. BLOCK Plant Pat. 2,230

STRAWBERRY PLANT

Filed April 10, 1961 2 Sheets-Sheet 1

Inventor

LOUIS H BLOCK

By Mark W. Gehan

Attorney

Feb. 26, 1963 L. H. BLOCK Plant Pat. 2,230

STRAWBERRY PLANT

Filed April 10, 1961 2 Sheets-Sheet 2

Inventor

LOUIS H BLOCK

By Mark W. Gehan

Attorney

United States Patent Office

Plant Pat. 2,230
Patented Feb. 26, 1963

2,230
STRAWBERRY PLANT
Louis H. Block, Ortonville, Minn.
Filed Apr. 10, 1961, Ser. No. 102,077
1 Claim. (Cl. 47—62)

This invention relates to a new and distinct variety of everbearing strawberry plant discovered by me on my farm at Ortonville, Minnesota, in the year 1956. The original plant colony, found by me in a cultivated area of my farm, presumably developed from a single seedling plant grown from a seed dropped by a bird. Plants were removed by me from the colony and planted in the garden in 1957. Since that time, the plant has been reproduced asexually by me on my farm each year by runner plants taken from the previous year's plantings. The plants have reproduced all plant and fruit characteristics true to type in each successive planting.

Figure 1:
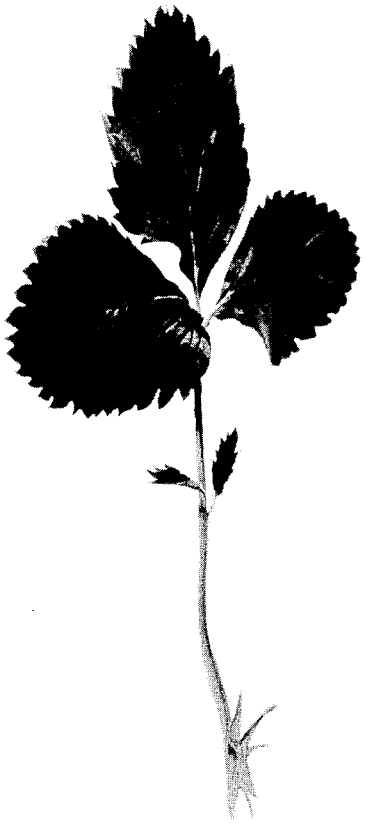
Figure 2:
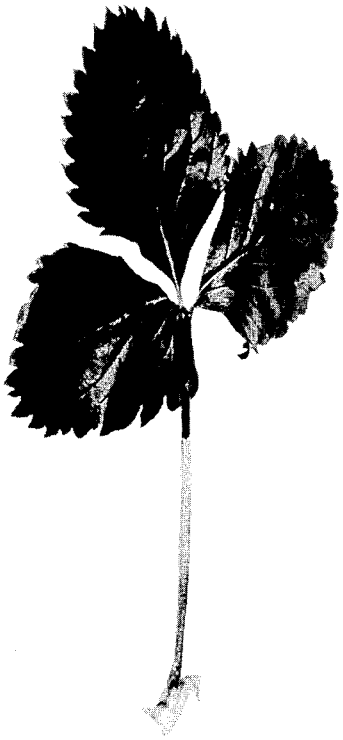

FIGURES 1 and 2 of the illustration accompanying these specifications show typical leaves from my new and distinct variety.

Figure 3:
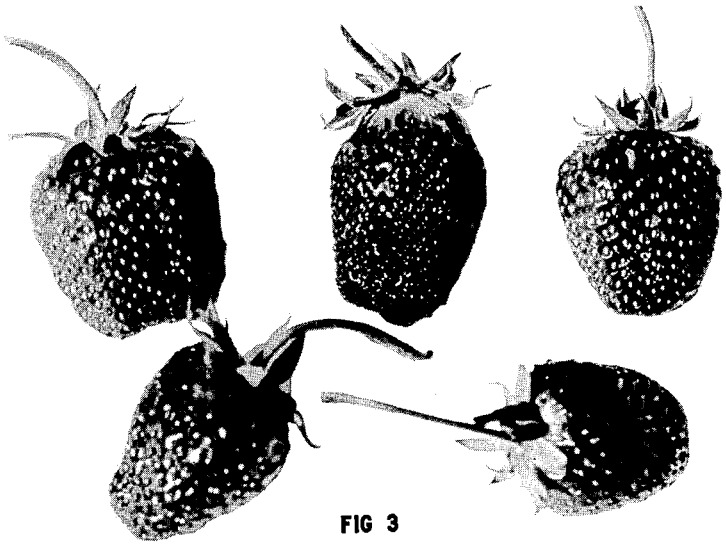

FIGURE 3 of the illustration shows five typical berries.

Figure 4:
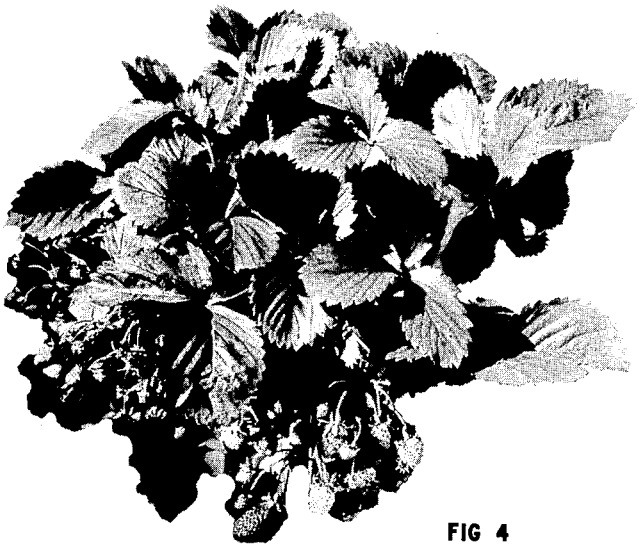

FIGURE 4 shows a typical plant structure.

*General Plant Characteristics*

The plants are very vigorous and form runners and runner plants freely. The runner internodes are medium in length and runner plants which develop at the nodes are spaced approximately six inches apart. On August 16, 1960, observations made on a new planting set on May 27, 1960, showed that runners from mother plants had developed from three to five new plants per runner with fruits or flower buds showing on each new plant.

This variety of strawberry is unusually productive. From a plantation of 66 plants set in the spring of 1959, a total crop of 57 quarts of fruits was harvested the same year from the combined mother and daughter plants. Such high yields are due to the prompt flowering and vigor of the young runner plants.

*Principal Distinguishing Characteristics*

The characteristics most useful in distinguishing this strawberry from other everbearing varieties are: (*a*) high productivity; (*b*) early formation of flowers on the runner plants; (*c*) the long-conic shape of the fruits with medium to distinct neck; (*d*) mild subacid flavor, and (*e*) numerous medium fine serrations on the leaflets. The combination of these characteristics and others as described below effectively distinguish this variety from any other known everbearing variety.

*Foliage*

The foliage is medium dense. The individual leaves are large; the leaflets are elliptic, with numerous small to medium sized serrations usually numbering ten to eleven on either side of the central leaflet. The upper surface is medium green, medium smooth, moderately pubescent, with depressed veins; the lower surface is light gray-green with moderate pubescence mainly along the veins. The petiole is green, medium in length and thickness, moderately pubescent over the entire length. Often one or two leaflets may develop along the upper half of the petiole, usually from one to two inches below the three normal leaflets.

*Flowers*

The flowers are medium in size, perfect, self-fertile, borne freely on young runner plants, often before rooting takes place.

*Fruit*

The fruit ripens early, about with Superfection or Gem, both unpatented. It is attractive, large to medium large in size. Typical shape is long conic to very long-conic with a small to medium neck. Under certain conditions during mid-summer the neck may become much enlarged and very prominent. Normally the length exceeds the diameter by 25 to 30 percent. Characteristically the fruits are smooth and regular without creases or ridges. Sometimes the larger berries are wedge-shaped and slightly irregular with a crease on the sides.

The outside color of the fruit is bright, attractive medium red. The inside color is medium red except for a lighter layer enclosing the core. A very small cavity in the core is often found in the large fruits. The flesh is tender, medium in firmness, medium juicy; flavor is pleasant, subacid, almost sweet, mildly aromatic; quality good to very good.

The achenes (seeds) are moderately conspicuous, small, set in depressions but projecting slightly above the surface of the fruit. The seeds are yellow but become red on the side of a fruit exposed to the sun.

The calyx is medium large, light green. The sepals are narrow and recurved. The calyx is easily removed because of the recurved sepals and rounded neck at the base of the fruit.

The fruit clusters are large, often carrying up to 15 to 20 fruits. Frequently one or more large leafy bracts with two stipule-like appendages are found at the place of first division of the fruiting stem. The peduncles are medium stout, medium long, heavily pubescent; the pedicels are long, medium thick moderately pubescent, easily snapped when berry is removed, resulting in easy picking.

All color designations throughout the specification are of ordinary dictionary meaning.

Having thus disclosed my invention, I claim:

A new and distinct variety of everbearing strawberry plant, substantially as herein shown and described, characterized particularly by its vigor and heavy production; its early formation of flowers on the runner plants; the long-conic shape of the fruits with medium to distinct neck; the mild subacid flavor of the fruit; and the numerous medium-fine serrations on the leaflets.

No references cited.